United States Patent
Kobayashi et al.

(10) Patent No.: US 12,152,154 B2
(45) Date of Patent: Nov. 26, 2024

(54) COATING COMPOSITION FOR APPLYING INKJET PRINTING THERETO TO FORM MARKED PREPARATION, PREPARATION MARKED WITH AQUEOUS INK, AND METHOD FOR PRODUCING MARKED PREPARATION

(71) Applicant: Shin-Etsu Chemical Co., Ltd., Tokyo (JP)

(72) Inventors: Aya Kobayashi, Yokohama (JP); Takafumi Hoshino, Yokohama (JP)

(73) Assignee: Shin-Etsu Chemical Co., Ltd., Tokyo (JP)

( * ) Notice: Subject to any disclaimer, the term of this patent is extended or adjusted under 35 U.S.C. 154(b) by 736 days.

(21) Appl. No.: 16/888,220

(22) Filed: May 29, 2020

(65) Prior Publication Data

US 2020/0385597 A1     Dec. 10, 2020

(30) Foreign Application Priority Data

Jun. 6, 2019   (JP) ................................. 2019-106514

(51) Int. Cl.
| | |
|---|---|
| C09D 11/54 | (2014.01) |
| B41J 3/407 | (2006.01) |
| B41M 5/00 | (2006.01) |
| C09D 5/16 | (2006.01) |
| C09D 11/033 | (2014.01) |
| C09D 11/106 | (2014.01) |
| C09D 11/14 | (2006.01) |
| C09D 11/30 | (2014.01) |
| C09D 101/02 | (2006.01) |
| C09D 101/26 | (2006.01) |

(52) U.S. Cl.
CPC .......... *C09D 101/26* (2013.01); *B41J 3/4073* (2013.01); *B41M 5/0017* (2013.01); *C09D 5/1668* (2013.01); *C09D 11/033* (2013.01); *C09D 11/106* (2013.01); *C09D 11/14* (2013.01); *C09D 11/30* (2013.01); *C09D 11/54* (2013.01); *C09D 101/02* (2013.01)

(58) Field of Classification Search
CPC ...... C09D 11/54; C09D 11/30; B41M 5/0011; B41M 5/0017; B41J 3/407; B41J 3/4073
See application file for complete search history.

(56) References Cited

U.S. PATENT DOCUMENTS

| | | | | |
|---|---|---|---|---|
| 4,917,885 A | * | 4/1990 | Chiba .................. | A61K 9/4816 206/530 |
| 2007/0132823 A1 | * | 6/2007 | Barreto .................. | C09D 11/30 347/100 |
| 2007/0134330 A1 | * | 6/2007 | Barreto ................ | A61K 9/2833 424/472 |
| 2012/0157580 A1 | * | 6/2012 | Yoshino ............... | C09D 101/28 524/43 |
| 2014/0199406 A1 | * | 7/2014 | Yokosawa ............ | A61K 9/5042 424/494 |
| 2020/0151413 A1 | | 5/2020 | Aoki et al. | |

FOREIGN PATENT DOCUMENTS

| | | | | |
|---|---|---|---|---|
| EP | 3216807 A1 | * | 9/2017 | ............. A61K 47/38 |
| JP | S61-100519 A | | 5/1986 | |
| JP | 2002003366 A | | 1/2002 | |
| JP | 2013253030 A | * | 12/2013 | |
| JP | 2015-140414 A | | 8/2015 | |
| WO | 2018/061989 A1 | | 4/2018 | |
| WO | 2018/199201 A1 | | 11/2018 | |

OTHER PUBLICATIONS

European Search Report for Application No. 20178218.2 dated Nov. 6, 2020.
Japanese Office Action dated Mar. 15, 2022 (Japanese).
Translation of Japanese Office Action dated Mar. 15, 2022 (English).
JPS61-100519A (Japanese) and U.S. Pat. No. 4,917,885 (English translation).
WO 2018/061989 A1 (Japanese) and machine translation (English).
WO 2018/199201 A1 (Japanese) and US 2020/0151413 A1 (English translation).
Japanese Office Action dated Mar. 15, 2022, Japanese Application No. 2019-106514.
English Translation of Japanese Office Action dated Mar. 15, 2022, Japanese Application No. 2019-106514.
Machine Translation of WO 2018/061989A1.
Communication pursuant to Article 94(3) EPC for European Application No. 20 178 218.2, dated Feb. 15, 2023 (5 pages).

* cited by examiner

*Primary Examiner* — Justin Seo
*Assistant Examiner* — Kendrick X Liu

(57) ABSTRACT

There are provided a coating composition for applying inkjet printing thereto to form a marked preparation, the composition providing good ink affinity, suppression of ink bleed, and excellent gloss; and others. More specifically, there are provided a composition for applying inkjet printing thereto to form a marked preparation, the composition including a water-soluble cellulose ether having a viscosity at 20° C. of from 2 to 50.0 mPa·s, as determined in 2% by mass aqueous solution, polyvinyl alcohol, and a solvent, wherein a mass ratio of the water-soluble cellulose ether to the polyvinyl alcohol is from 99.0:1.0 to 55.0:45.0; a method for producing a preparation marked with aqueous ink, including a coating step of coating an object with the composition to form a coating layer, and a printing step of inkjet-printing on the coating layer with aqueous ink to obtain a preparation marked with aqueous ink; and others.

9 Claims, No Drawings

COATING COMPOSITION FOR APPLYING INKJET PRINTING THERETO TO FORM MARKED PREPARATION, PREPARATION MARKED WITH AQUEOUS INK, AND METHOD FOR PRODUCING MARKED PREPARATION

CROSS REFERENCE TO RELATED APPLICATIONS

The present application is a Non-provisional application, which claims priority to Japanese Application No. 2019-106514 filed Jun. 6, 2019, the contents of the above application are incorporated by reference herein in their entireties.

BACKGROUND OF THE INVENTION

1. Field of the Invention

The invention relates to a coating composition for applying inkjet printing thereto to form a marked preparation, a preparation marked with aqueous ink, and a method for producing the preparation marked with aqueous ink.

2. Related Art

It is desired to develop a dosage form having excellent visual distinctiveness in order to improve compliance of medication, while preventing dispensing errors, medication mistakes, and administration of counterfeit drugs in the medical field. Typical dosage forms for enhancing discrimination include, for example, engraved tablets. However, there remain problems of abrasiveness of the engraved portions and difficulty in discriminating the engraved tablets due to filling of the engraved portions during film coating on the engraved tablets.

To avoid these problems, it is known to print a bar code, a product name, or a product code on a medical preparation to improve discrimination. Examples of such a printing are known to include a contact type printing such as offset printing and gravure printing, and a non-contact type printing such inkjet printing and UV laser printing. For example, by using a tablet printing apparatus adapted for an inkjet method, it is possible to clearly print an image on a surface of the tablet without applying pressure to the surface.

Types of inks used in the inkjet printing include a dye ink and a pigment ink. The dye ink has a dye dissolved in an ink liquid so that separation and precipitation in the container or the liquid line are small. However, the dye ink has a disadvantage of fading by light. On the other hand, the pigment ink is less likely to discolor or fade than the dye ink so that it is desirable to use the pigment ink for a medical preparation to have high resistance to light. For example, as a pigment-ink-containing composition for tablet printing, there has been proposed an ink composition, comprising an edible pigment, water, a lower alcohol, a dispersant, and a plasticizer (JP2015-140414A).

SUMMARY OF THE INVENTION

However, some examples of the ink composition proposed in JP2015-140414A result in low ink affinity of the surface of the preparation and/or ink bleed.

The invention has been made in view of the above circumstances, and an object of the invention is to provide a coating composition for applying inkjet printing thereto to form a marked preparation, the composition providing good ink affinity, suppression of ink bleed, and excellent gloss; a preparation marked with aqueous ink; and a method for producing the preparation marked with aqueous ink.

As a result of intensive investigation to achieve the above-mentioned object, the inventors have found that by using a coating composition containing a water-soluble cellulose ether and polyvinyl alcohol at a specified ratio, the inkjet printing on the formed coating layer results in a marked preparation having good ink affinity, suppression of ink bleed, and excellent gloss because the coated preparation has; and the invention has been made.

In one aspect of the invention, there is provided a coating composition for applying ink jet printing thereto to form a marked preparation, the composition comprising:
- a water-soluble cellulose ether having a viscosity at 20° C. of from 2 to 50.0 mPa·s, as determined in a 2% by mass aqueous solution thereof;
- polyvinyl alcohol; and
- a solvent;

wherein a mass ratio of the water-soluble cellulose ether to the polyvinyl alcohol is from 99.0:1.0 to 55.0:45.0.

In another aspect of the invention, there is provided a method for producing a preparation marked with aqueous ink, comprising:
- a coating step of coating an object with the composition to form a coating layer on the object; and
- a printing step of inkjet-printing on the coating layer with aqueous ink to obtain a preparation marked with the aqueous ink.

In still another aspect of the invention, there is provided a preparation marked with aqueous ink, the preparation comprising:
- a coating layer comprising a water-soluble cellulose ether having a viscosity at 20° C. of from 2 to 50.0 mPa·s, as determined in a 2% by mass aqueous solution, and polyvinyl alcohol, wherein a mass ratio of the water-soluble cellulose ether to the polyvinyl alcohol is from 99.0:1.0 to 55.0:45.0; and
- a mark with aqueous ink on the coating layer.

According to the invention, inkjet printing on the coating layer of the preparation can easily provide a preparation marked with aqueous ink, the marked preparation having good ink affinity and suppression of ink bleed, and excellent gloss. In addition, since the coating layer of the preparation has good ink affinity, the drying time after inkjet printing can be expected to be shortened. Furthermore, the presence of the water-soluble cellulose ether can reduce tackiness and adhesiveness of the polyvinyl alcohol during coating, so that the improvement of the spray rate can also be expected.

DETAILED DESCRIPTION OF THE PREFERRED EMBODIMENTS

There will be described the coating composition for applying inkjet printing thereto to form a marked preparation, the composition comprising a water-soluble cellulose ether having a viscosity at 20° C. of from 2.0 to 50.0 mPa·s, as determined in a 2% by mass aqueous solution thereof, polyvinyl alcohol, and a solvent, wherein the mass ratio of the water-soluble cellulose ether to the polyvinyl alcohol is from 99.0:1.0 to 55.0:45.0.

The water-soluble cellulose ether is a nonionic polymer having the hydroxyl groups of cellulose partially etherified. Examples of the water-soluble cellulose ether include an alkyl cellulose, a hydroxyalkyl cellulose, and a hydroxyalkyl alkyl cellulose.

Examples of the alkyl cellulose include methylcellulose. The content of methoxy groups in the methylcellulose is preferably from 26.0 to 33.0% by mass, more preferably from 27.5 to 31.5% by mass. The content of the methoxy groups in the methylcellulose may be measured in accordance with the assay for methylcellulose in the Japanese Pharmacopoeia Seventeenth Edition.

Examples of the hydroxyalkyl cellulose include hydroxypropyl cellulose. The content of hydroxypropoxy groups in the hydroxypropyl cellulose is preferably from 53.4 to 80.5% by mass, more preferably from 60.0 to 70.0% by mass. The content of the hydroxypropoxy groups in the hydroxypropyl cellulose may be measured in accordance with the assay for hydroxypropyl cellulose in the Japanese Pharmacopoeia Seventeenth Edition.

Examples of the hydroxyalkyl alkyl cellulose include hydroxypropyl methylcellulose (hereinafter also referred to as "HPMC"). The content of methoxy groups in HPMC is preferably from 16.5 to 30.0% by mass, more preferably from 28.0 to 30.0% by mass, from the viewpoint of providing a good coating layer (coat or film). The content of hydroxypropoxy groups in HPMC is preferably from 4.0 to 32.0% by mass, more preferably from 7.0 to 12.0% by mass, from the viewpoint of providing a good coating layer (coat or film). The content of hydroxypropoxy groups and the content of methoxy groups in HPMC may be measured by the quantitative method described in "Hypromellose: hydroxypropyl methyl cellulose" of the Japanese Pharmacopoeia Seventeenth Edition.

As the water-soluble cellulose ether, a hydroxyalkyl alkyl cellulose such as HPMC having a methoxy group content of preferably from 16.5 to 30.0% by mass and a hydroxypropoxy group content of preferably from 4.0 to 32.0% by mass is preferable from the viewpoint of providing a good coating layer (coat or film).

The viscosity at 20° C. of a 2% by mass aqueous solution of the water-soluble cellulose ether is from 2.0 to 50.0 mPa·s, preferably from 2.0 to 25.0 mPa·s, more preferably from 5.0 to 7.0 mPa·s. When the viscosity is less than 2.0 mPa·s, the polymerization degree of the water-soluble cellulose ether is extremely low so that the strength of the coating layer (coat or film) may not be maintained. On the other hand, when the viscosity is more than 50.0 mPa·s, the concentration of the water-soluble cellulose ether in the coating composition have to be kept low so that the coating operation takes a long time, thereby preventing the efficient production. The viscosity at 20° C. of a 2% by mass aqueous solution of the water-soluble cellulose ether may be measured by using a Ubbelohde-type viscometer in accordance with the viscosity measurement by capillary tube viscometer of the Viscosity Determination in the General Tests of the Japanese Pharmacopoeia. Seventeenth Edition.

If necessary, two or more types of the water-soluble cellulose ether may be combined. A commercially available water-soluble cellulose ether may be used.

A degree of saponification of polyvinyl alcohol (hereinafter also referred to as "PVA") is preferably 74.0 mol % or more, more preferably from 78.0 to 99.5 mol %, and still more preferably from 85.0 to 89.0 mol %, from the viewpoint of moisture resistance of the coating layer (coat or film). A degree of saponification of PVA may be measured according to the method of measuring a degree of saponification described in JIS K6726 (1994).

The viscosity at 20° C. of a 4% by mass aqueous solution of polyvinyl alcohol is preferably from 2.0 to 100.0 mPa·s, more preferably from 3.0 to 50.0 mPa·s, from the viewpoint of providing a good coating layer (coat or film). The viscosity at 20° C. of a 4% by mass aqueous solution of polyvinyl alcohol may be determined in accordance with the method of measuring a viscosity described in JIS K6726.

If necessary, two or more types of polyvinyl alcohol may be combined. A commercially available polyvinyl alcohol may be used.

The mass ratio of the water-soluble cellulose to the polyvinyl alcohol in the coating composition is from 99.0:1.0 to 55.0:45.0, preferably from 98.0:2.0 to 75.0:25.0, more preferably from 97.0:3.0 to 90.0:10.0. When the mass ratio of the water-soluble cellulose ether is less than 55.0, the initial ink affinity is inferior, and the ink bleed cannot be reduced. When the mass ratio of the polyvinyl alcohol is more than 45.0, the ink bleed cannot be reduced.

Examples of the solvent include water and lower alcohols having 1 to 3 carbon atoms. The solvent may be a mixed solvent of water and a lower alcohol having 1 to 3 carbon atoms. Examples of the water include purified water. Examples of the lower alcohols having 1 to 3 carbon atoms include ethanol, methanol, and isopropyl alcohol. As the solvent, water is preferable from the viewpoint of safety and handleability during coating.

If necessary, two or more types of solvents may be combined. A commercially available solvent may be used. The solvent content in the coating composition is preferably from 200 to 1500 parts by mass, more preferably from 800 to 1400 parts by mass, relative to 100 parts by mass of the sum of the water-soluble cellulose ether and PVA from the viewpoint of handleability and workability during coating.

The coating composition may comprise an optional additive. Example of the additive include a plasticizer, a lubricant, a brightener, a surfactant, a colorant, an edible pigment, a sweetener, a coating agent, and an antifoaming agent.

Examples of the plasticizer include glycerin, polyethylene glycol, propylene glycol, and triethyl citrate.

Examples of the lubricant include talc, magnesium stearate, calcium stearate, colloidal silica, and stearic acid.

Examples of the brightener include a carnauba wax, a shellac, a beeswax, a hardened oil, and magnesium stearate.

Examples of the surfactant include polysorbate 80, polysorbate 60, sucrose fatty acid ester, macrogol 400, sodium lauryl sulfate, polyoxyl stearate 40, and polyoxyethylene hardened castor oil 60.

Examples of the colorant include yellow iron oxide, diiron trioxide (red), orange essence, brown iron oxide, caramel, light anhydrous silicic acid, food blue No. 5, food yellow No. 4, food yellow No. 4 aluminum lake, food yellow No. 5, food red No. 2, food red No. 3, food red No. 102, food blue No. 2, talc, fluorescein sodium, green tea powder, vitamin C, food lake coloring, carotenoid-based dyes, flavonoid-based dyes, and quinone-based dyes.

Examples of the edible pigment include carbon black, food red No. 2 aluminum lake, food red No. 3 aluminum lake, food red No. 40 aluminum lake, food yellow No. 4 aluminum lake, food yellow No. 5 aluminum lake, food blue No. 1 aluminum lake, food blue No. 2 aluminum lake, diiron trioxide, yellow diiron trioxide, and black iron oxide.

Examples of the sweetener include acesulfame potassium, sucralose, palatinose, maltose, and xylitol.

Examples of the coating agent include gum arabic, ethylcellulose, hydroxypropyl cellulose, carboxyvinyl polymer, and carboxymethylethylcellulose.

Examples of the antifoaming agent include glycerin fatty acid esters, dimethylpolysiloxane, silicon dioxide mixtures, and sucrose fatty acid esters.

The content of the additive in the coating composition is not particularly limited. It is preferably 200 parts by mass or less, more preferably from 0 to 100 parts by mass, relative to 100 parts by mass of the sum of the water-soluble cellulose ether and PVA.

The coating composition may be produced in a step of mixing a water-soluble cellulose ether having a viscosity at 20° C. of from 2.0 to 50.0 mPa·s, as determined in a 2% by mass aqueous solution thereof, polyvinyl alcohol, a solvent, and an optional additive to obtain a coating composition.

The method of mixing a water-soluble cellulose ether having a viscosity at 20° C. of from 2.0 to 50.0 mPa·s, as determined in a 2% by mass aqueous solution thereof, polyvinyl alcohol, a solvent, and an optional additive is not particularly limited. For example, it is preferable to use a method for producing a coating composition comprising steps of: mixing a polyvinyl alcohol and a solvent to obtain a polyvinyl alcohol solution, and then mixing the polyvinyl alcohol solution with a water-soluble cellulose, from the viewpoint of preventing the lump formation and gelation of the water-soluble cellulose ether and the polyvinyl alcohol.

In the step of mixing polyvinyl alcohol and a solvent to obtain a polyvinyl alcohol solution, it is preferable to disperse the polyvinyl alcohol in the solvent of preferably from 20 to 30° C., and then heat the resulting dispersion to preferably 50 to 80° C. with mixing to dissolve the polyvinyl alcohol to obtain a polyvinyl alcohol solution.

In the step of mixing the polyvinyl alcohol solution with a water-soluble cellulose to obtain a coating composition, it is preferable to disperse a water-soluble cellulose ether in the polyvinyl alcohol solution of 70 to 90° C., and then cool the resulting dispersion to 15 to 30° C. with mixing to dissolve the water-soluble cellulose ether to obtain a coating composition.

Mixing of a water-soluble cellulose ether having a viscosity at 20° C. of from 2.0 to 50.0 mPa·s, as determined in a 2% by mass aqueous solution thereof, polyvinyl alcohol, a solvent, and an optional additive may be carried out with a stirrer. The mixing time is not particularly limited as long as the water-soluble cellulose ether having a viscosity at 20° C. of from 2.0 to 50.0 mPa·s, as determined in a 2% by mass aqueous solution thereof, and the polyvinyl alcohol can be dissolved in the solvent.

Next, there will be described a method for producing a preparation marked with aqueous ink, comprising a coating step of coating an object with the above-mentioned coating composition to form a coating layer; and a printing step of inkjet-printing on the coating layer with aqueous ink to obtain a preparation marked with aqueous ink.

The coating step in the method for producing a preparation inkjet-printed with aqueous ink will be described. The object to be coated is preferably a core comprising an active ingredient or a mold pin for capsule formation. More specifically, the coating step preferably comprises coating a core comprising an active ingredient with the above-mentioned coating composition, or coating a molding pin for capsule formation with the above-mentioned coating composition.

An embodiment in which a core containing an active ingredient is coated with the above-mentioned coating composition will be described.

The active ingredient may be any active ingredient that can be orally administered. Examples of the active ingredient include drugs used in pharmaceutical products and active ingredients used in health foods such as foods with nutrient function claims, foods for specified health use, and foods with functional claims.

Example of the drug used in pharmaceutical products include a drug for the central nervous system, a drug for the cardiovascular system, a drug for the respiratory system, a drug for the digestive system, an antibiotic, an antitussive and expectorant, an antihistamine, an antipyretic anti-inflammatory analgesic, a diuretic, an autonomic agent, an antimalarial agent, an antidiarrheal agent, a psychotropic, and vitamins and derivatives thereof.

Examples of the drug for the central nervous system include diazepam, idebenone, naproxen, piroxicam, indomethacin, sulindac, lorazepam, nitrazepam, phenytoin, acetaminophen, ethenzamide, ketoprofen, and chlordiazepoxide.

Examples of the drug for the cardiovascular system include molsidomine, vinpocetine, propranolol, methyldopa, dipyridamole, furosemide, triamterene, nifedipine, atenolol, spironolactone, metoprolol, pindolol, captopril, isosorbide dinitrate, delapril hydrochloride, meclofenoxate hydrochloride, diltiazem hydrochloride, etilefrine hydrochloride, digitoxin, and alprenolol hydrochloride.

Examples of the drug for the respiratory system include amlexanox, dextromethorphan, theophylline, pseudoephedrine, salbutamol, and guaifenesin.

Examples of the drug for the digestive system include a benzimidazole drug having antiulcer action, such as 2-[[3-methyl-4-(2,2,2-trifluoroethoxy)-2-pyridyl]methylsulfinyl]benzimidazole and 5-methoxy-2-[(4-methoxy-3,5-dimethyl-2-pyridyl)methylsulfinyl]benzimidazole; cimetidine; ranitidine; pirenzepine hydrochloride; pancreatin; bisacodyl; and 5-aminosalicylic acid.

Examples of the antibiotic include talampicillin hydrochloride, bacampicillin hydrochloride, cefaclor, and erythromycin.

Examples of the antitussive and expectorant include noscapine hydrochloride, carbetapentane citrate, isoaminile citrate, and dimemorfan phosphate.

Examples of the antihistamine include chlorpheniramine maleate, diphenhydramine hydrochloride, and promethazine hydrochloride.

Examples of the antipyretic anti-inflammatory analgesic include ibuprofen, diclofenac sodium, flufenamic acid, sulpyrine, aspirin, and ketoprofen.

Examples of the diuretic include caffeine.

Examples of the autonomic agent include dihydrocodeine phosphate, dl-methylephedrine hydrochloride, atropine sulfate, acetylcholine chloride, and neostigmine.

Examples of the antimalarial agent include quinine hydrochloride.

Examples of the antidiarrheal agent include loperamide hydrochloride.

Examples of the psychotropic include chlorpromazine.

Examples of the vitamins and derivatives thereof include vitamin A, vitamin B1, fursultiamine, vitamin B2, vitamin B6, vitamin B12, vitamin C, vitamin D, vitamin E, vitamin K, calcium pantothenate, and tranexamic acid.

Examples of the active ingredient used in the health food include the above vitamins and derivatives thereof, minerals, carotenoids, amino acids and derivatives thereof, plant extracts, and health food materials.

Examples of the mineral include calcium, magnesium, manganese, zinc, iron, copper, selenium, chromium, sulfur, and iodine.

Examples of the carotenoid include β-carotene, α-carotene, lutein, cryptoxanthin, zeaxanthin, lycopene, astaxanthin, and multicarotene.

Examples of the amino acid include an acidic amino acid, a basic amino acid, a neutral amino acid, and an acidic amino acid amide.

Examples of the acidic amino acid include aspartic acid and glutamic acid.

Examples of the basic amino acid include lysine, arginine, and histidine.

Examples of the neutral amino acid include linear aliphatic amino acids such as alanine and glycine; branched aliphatic amino acids such as valine, leucine and isoleucine; hydroxyamino acids such as serine and threonine; sulfur-containing amino acids such as cysteine and methionine; aromatic amino acids such as phenylalanine and tyrosine; heterocyclic amino acids such as tryptophan; and imino acids such as proline.

Examples of the acidic amino acid amide include asparagine and glutamine.

Examples of the amino acid derivative include acetylglutamine, acetylcysteine, carboxymethylcysteine, acetyltyrosine, acetylhydroxyproline, 5-hydroxyproline, glutathione, creatine, S-adenosylmethionine, glycylglycine, glycylglutamine, dopa, alanylglutamine, carnitine and γ-aminobutyric acid.

Examples of the plant extract include aloe extract, propolis extract, agaricus extract, Panax ginseng extract, ginkgo leaf extract, turmeric extract, curcumin, sprouted brown rice extract, shiitake mycelium extract, Rubus suavissimus extract, sweet Hydrangea leaf extract, Fomes yucatensis extract, sesame extract, garlic extract, maca (*Lepidium meyenii*) extract, plant worm (*Cordyceps sinensis*) extract, camomile extract, and red pepper extract.

Examples of the health food material include royal jelly; dietary fibers; proteins; bifidobacteria; lactic acid bacteria; chitosan; yeast; glucosamine; lecithin; polyphenols; cartilage of animals, fish and shellfish; soft-shelled turtle; lactoferrin; freshwater clams; eicosapentaenoic acid; germanium; enzymes; creatine; carnitine; citric acid; raspberry ketone; coenzyme Q10; methylsulfonylmethane; and soybean peptides bonded with phospholipids.

An amount of the active ingredient may be appropriately determined depending on the type of preparation. If necessary, two or more types of active ingredients may be combined. A commercially available active ingredient may be used.

The core comprising the active ingredient may comprise an optional additive such as an excipient, a binder, a disintegrant, a lubricant, a fluidizing agent, a colorant, and a dissolution aid for a pharmaceutical compound.

Examples of the excipient include saccharides such as white soft sugar, lactose, mannitol and glucose; starches; crystalline cellulose; calcium phosphate; and calcium sulfate.

Examples of the binder include polyvinyl alcohol; polyacrylic acid; polymethacrylic acid; polyvinylpyrrolidone; glucose; white soft sugar; lactose; maltose; dextrin; sorbitol; mannitol; hydroxyethyl cellulose; hydroxypropyl methylcellulose; hydroxypropyl cellulose; macrogols such as macrogol 4000, macrogol 6000 and macrogol 20000; gum arabic; gelatine; agar; starches such as corn starch.

Examples of the disintegrant include low-substituted hydroxypropyl cellulose, carmellose or a salt thereof, croscarmellose sodium, sodium carboxymethyl starch, crospovidone, crystalline cellulose, and crystalline cellulose-carmellose sodium.

Examples of the lubricant include talc, magnesium stearate, calcium stearate, colloidal silica, stearic acid, waxes, hardened oils, polyethylene glycols, and sodium benzoate.

Examples of the fluidizing agent include hydrated silicon dioxide, light anhydrous silicic acid, and titanium oxide.

Examples of the colorant include yellow diiron trioxide, diiron trioxide, food blue No. 1, food blue No. 2, food yellow No. 4, food yellow No. 5, food green No. 3, food red No. 2, food red No. 3, food red No. 102, food red No. 104, food red No. 105, and food red No. 106.

Examples of the solubilizing agent for a pharmaceutical compound include organic acids such as fumaric acid, succinic acid, malic acid and adipic acid.

An amount of the additive may be appropriately selected depending on a type of the preparation. If necessary, two or more types of additives may be combined. A commercial additive may be used.

The shape (dosage form) of the core comprising an active ingredient is not particularly limited. Example of the core include oral solid preparations such as a tablet, powder, a granule, a fine granule, a pill, a troche, and a capsule. Among these, the tablet is particularly preferable.

Examples of the tablet include an uncoated tablet, a dragee; a gelatine-encapsulated tablet; a film-coated tablet including a multilayer film-coated tablet; an enteric-coated tablet; and a nucleated tablet such as a compression-encapsulated tablet.

The core comprising an active ingredient may be subjected to an optional undercoating step prior to the coating step of coating with the coating composition. In the undercoating step, the core may be coated with a coating base material such as hydroxypropyl methylcellulose.

The core comprising an active ingredient may be coated by using a coating apparatus or the like. Examples of the coating apparatus include a pan coating apparatus, a drum type coating apparatus, a fluidized bed coating apparatus, and a stirring flow coating apparatus.

Examples of the spray device to be used together with the coating apparatus may include an air spray, an airless spray, and a three-fluid spray.

After coating, optional drying may be carried out.

An amount of the coating composition to be coated on the surface of the core comprising an active ingredient may be appropriately selected in consideration of the type, shape, size, and surface conditions of the core (preparation), as well as nature of the drug and additive contained in the core (preparation). For example, when the shape (dosage form) of the core comprising an active ingredient is a tablet, it is preferably from 1 to 10 parts by mass, more preferably from 1 to 7 parts by mass, and particularly preferably from 2 to 6 parts by mass, relative to 100 parts by mass of the tablet.

The thickness of the coating layer in the tablet is preferably from 20 to 30 μm from the viewpoint of forming a uniform continuous coating layer. The thickness of the coating layer in the tablet may be measured using a Digital Microscope VHX-2000 (produced by Keyence Corporation).

Next, there will be described an embodiment in which a mold pin for capsule formation is coated with the above-mentioned coating composition.

The coating of the mold pin for capsule formation with the coating composition may be carried out by dipping the mold pin into the coating composition and taking it out of the composition.

The coating of the mold pin for capsule formation with the above-mentioned coating composition may be carried out by using a cold pin method or a hot pin method. In the cold pin method, a mold pin of 5 to 20° C. is dipped into the coating composition containing a gelling agent such as guar gum or xanthan gum. In the hot pin method, a mold pin of 40 to 95° C. is dipped into the coating composition containing no gelling agent.

Subsequently, a capsule may be produced by drying the composition adhered to the mold pin for capsule formation to form a coating layer (coat or film), and removing the coating layer (coat or film) from the mold pin. Then the coating layer (coat or film) is cut and combined to form a capsule.

Next, there will be described a printing step in the method for producing a preparation marked with aqueous ink. Known aqueous ink may be used. For example, the aqueous ink may comprise a colorant (coloring matter) and a solvent which is a mixture of water and a lower alcohol having 1 to 3 carbon atoms.

The colorant is preferably edible. Examples of the colorant include a pigment and a dye.

Examples of the pigment include vegetable carbon black, carbon black, food red No. 2 aluminum lake, food red No. 3 aluminum lake, food red No. 40 aluminum lake, food yellow No. 4 aluminum lake, food yellow No. 5 aluminum lake, food blue No. 1 aluminum lake, food blue No. 2 aluminum lake, diiron trioxide, yellow diiron trioxide, and black iron oxide.

Examples of the vegetable carbon black include bamboo charcoal, cedar charcoal, and coconut shell charcoal.

Examples of the dye include an edible synthetic dye, and an edible natural dye.

If necessary, two or more types of colorants may be combined. A commercially available colorant may be used. The content of the colorant in the aqueous ink is preferably from 5 to 15% by mass from the viewpoint of marking on the coating layer formed by the coating composition.

Examples of the lower alcohol having 1 to 3 carbon atoms include ethanol, methanol, and isopropyl alcohol. If necessary, the lower alcohol having 1 to 3 carbon atoms may be used in combination of two or more types. Commercially available lower alcohol having 1 to 3 carbon atoms may be used. The content of the lower alcohol having 1 to 3 carbon atoms in the aqueous ink is preferably from 5 to 60% by mass, more preferably from 20 to 40% by mass, from the viewpoint of stability and dryness of the aqueous ink.

Examples of the water include purified water. The content of the water in the aqueous ink is preferably from 25 to 90% by mass, more preferably from 50 to 80% by mass, from the viewpoint of the safety and handleability of the aqueous ink.

The ink jet printing with aqueous ink may be carried out by a known method.

Before the ink-jet printing, a coating treatment using a brightener may be carried out on the coating layer (coat or film) to the extent that the effect of the invention is not impaired. Examples of the brightener include a carnauba wax, and a white beeswax.

As described above, a preparation comprising the coating layer formed from the above-mentioned coating composition and a mark with aqueous ink on the coating layer can be produced. Examples of the preparation include a tablet and a capsule. Since an volatile component such as the solvent is removed, the coating layer formed from the above-mentioned coating composition comprises a water-soluble cellulose ether having a viscosity at 20° C. of from 2.0 to 50.0 mPa·s, as determined in a 2% by mass aqueous solution thereof, and polyvinyl alcohol, wherein a mass ratio of the water-soluble cellulose ether to the polyvinyl alcohol is from 99.0:1.0 to 55.0:45.0.

For example, there can be produced a preparation comprising a core comprising an active ingredient, a coating layer on the core, and a mark with aqueous ink on the coating layer. When the coating layer is a capsule shell, and a capsule comprising a mark with aqueous ink on the capsule shell can be produced.

A type of the mark with aqueous ink is not particularly limited as long as it can be printed by inkjet printing. Example of the mark include a letter and a figure such as identification code and symbol.

EXAMPLES

The invention will be described with reference to Examples and Comparative Examples below. It should not be construed that the invention is limited to or by them.

Example 1

An aqueous solution of polyvinyl alcohol was prepared by dispersing 1.5 g of polyvinyl alcohol (a degree of saponification of 88.0 mol %, a viscosity at 20° C. of 5.30 mPa·s, as determined in an 4% by mass aqueous solution thereof, and product of Japan VAM & PVA Co., Ltd.) in 270 g of purified water at 560 rpm with a stirrer (lab stirrer LT-400D, produced by Yamato Scientific Co., Ltd.) at 25° C. for 2 minutes, and then dissolving the polyvinyl alcohol in the purified water at 560 rpm at 60° C. for 6 minutes.

While stirring the aqueous solution of polyvinyl alcohol at 560 rpm with a stirrer (lab stirrer LT-400D, produced by Yamato Scientific Co., Ltd.) at 80° C., 28.5 g of HPMC (content of methoxy groups of 28.8% by mass, content of hydroxypropoxy groups of 8.8% by mass, and a viscosity at 20° C. of 5.91 mPa·s, as determined in a 2% by mass aqueous solution thereof) was added thereto, dispersed therein with stirring at 560 rpm at 80° C. for 3 minutes, and then dissolved therein with stirring at 560 rpm at 20° C. for 5 minutes to produce a coating composition for applying ink-jet printing thereto to form a marked preparation.

The 100 parts by mass of an uncoated tablet was coated with the obtained coating composition to form a coating layer having 3 parts by mass of solid content (i.e. content of the sum of HPMC and PVA) under the coating conditions below. The coating layer was dried in the same apparatus at a supply air temperature of 50 to 60° C. and a pan revolution speed of 18 rpm for 30 minutes without spraying the coating composition, thereby forming a tablet having the coating layer thereon.

<Composition of Uncoated Tablet>
  Lactose: 80.7% by mass (Pharmatose® 200M, produced by DFE Pharma)
  Corn starch: 9.0% by mass (Corn Starch, produced by Nihon Shokuhin Kako Co., Ltd.)
  HPMC: 2.9% by mass (methoxy group content of 28.9% by mass, hydroxypropoxy group content of 8.9% by mass, and viscosity at 20° C. of 5.91 mPa·s, as determined in a 2% by mass aqueous solution)
  Light anhydrous silicic acid: 3.9% by mass (Adsolider (registered trademark) 101, produced by Freund Corporation)
  Low-substituted hydroxypropyl cellulose (hereinafter also referred to as "L-HPC"): 3.0% by mass (hydroxypropoxy group content of 11% by mass)
  Magnesium stearate: 0.5% by mass (Magnesium stearate, produced by Taihei Chemical Industrial Co., Ltd.)

<Shape and Mass of Tablet>
  Tablet shape: diameter of 8.0 mm and curvature radius of 6.5 mm
  Tablet mass: 190 mg/tablet <Coating Conditions>
  Apparatus: perforated pan coater (HICOATER FZ LABO having a coating pan with an inside diameter of 30 cm, produced by Freund Corporation)

Amount of uncoated tablets: 1 kg
Supply air temperature: 50 to 60° C.
Discharge air temperature: 25 to 30° C.
Intake air flow: 0.6 m³/min
Pan revolutions: 18 rpm
Spray rate: 5.0 to 6.0 g/min
Spray air pressure: 150 kPa
Nozzle diameter: 1.0 mm The ink affinity, ink bleed, and glossiness of the coating layer on the tablet were evaluated under the following conditions. The ink affinity was evaluated by observing the contact angle and the timewise change ratio of contact angles of ink droplet. The ink bleed was evaluated by observing the timewise change ratio of the contact widths of ink droplet. The thickness of the coating layer was 25 μm. The glossiness was evaluated with respect to the coating layer before inkjet printing.

<Thickness Measurement Conditions>
  Apparatus: Digital Microscope VHX-2000 (produced by Keyence Corporation)
  Measurement: The thickness of the coating film was measured by observing the cross-section of the coated tablet.

<Composition of Aqueous Ink>
  The composition of each aqueous ink is described in Tables 1 and 2. As the bamboo charcoal, "food color black" (produced by Kyoritsu-Food Co., Ltd.) was used.

<Contact Angle Measurement Conditions>
  Apparatus: Contact Angle and Surface Tension Measuring Appartus FTA1000 (produced by First Ten Angstroms, Inc.)
  Droplet size: 2 μL
  Measurement time: 50 seconds
  Temperature: 25° C.
  Humidity: 40%

The "initial contact angle" refers to the contact angle of ink droplet measured at the time when the ink droplet and the coating layer of the coated tablet first come into contact with each other. That is, it is the contact angle after 0 seconds. The timewise change ratio of contact angles is calculated by the following equation.

Time wise change ratio of contact angles=(initial contact angle−contact angle at the end of measurement)×100/initial contact angle Furthermore, the "initial contact width" refers to the contact width of ink droplet measured at the time when the ink droplet and the coating layer of the tablet first come into contact. That is, it is the contact width after 0 second. The timewise change ratio of contact widths is calculated by the following equation.

Timewise change ratio of contact widths=(contact width at the end of measurement−initial contact width)×100/initial contact width <Evaluation Criteria for Contact Angle>
As the evaluation based on each evaluation criterion below, "good", "ordinary" and "bad" are assigned.
Initial Contact Angle
  good: 80° or more
  ordinary: 60° or more and less than 80°
  bad: less than 60°
Timewise Change Ratio of Contact Angles
  good: 20% or more
  ordinary: 16% or more and less than 20%
  bad: less than 16%
Initial Contact Width
  good: 0.65 μm or less
  ordinary: more than 0.65 μm and not more than 0.75 μm
  bad: more than 0.75 μm
Timewise Change Ratio of Contact Widths
  good: less than 20%
  ordinary: 20% or more and less than than 21%
  bad: 21% or more <Gloss Measurement Conditions>
  Apparatus: Digital Gloss Meter GM-26D (Murakami Color Research Laboratory)
  Angle of incidence: 60°

<Evaluation Criteria for Glossiness>
  good: 4.5 or more
  ordinary: 4.0 or more and less than 4.5
  bad: less than 4.0

Examples 2 to 3 and Comparative Examples 1 to 3

A coating composition for applying inkjet printing thereto to form a marked preparation was produced, an uncoated tablet was coated with the composition, and the coated tablet was evaluated in terms of the ink affinity, ink bleed, and glossiness in the same manner as in Example 1, except that the composition for coating a preparation was changed to those described in Table 1. The results are shown in Tables 1 and 2.

TABLE 1

| | coating composition for applying inkjet printing thereto | | | | | | aqueous ink | | | | |
|---|---|---|---|---|---|---|---|---|---|---|---|
| | water-soluble | | | | | | | | | | |
| | cellulose ether | | PVA | solvent | | | colorant | | lower alcohol | | water |
| | type | content (mass %) | content (mass %) | type | content (mass %) | mass ratio of HPMC:PVA | type | content (mass %) | type | content (mass %) | content (mass %) |
| Example 1 | HPMC | 9.50 | 0.50 | water | 90.0 | 95.0:5.0 | bamboo charcoal | 10 | ethanol | 27 | 63 |
| Example 2 | HPMC | 7.78 | 2.22 | water | 90.0 | 77.8:22.2 | bamboo charcoal | 10 | ethanol | 27 | 63 |
| Example 3 | HPMC | 5.50 | 4.50 | water | 90.0 | 55.0:45.0 | bamboo charcoal | 10 | ethanol | 27 | 63 |
| Comp. Ex. 1 | HPMC | 5.00 | 5.00 | water | 90.0 | 50.0:50.0 | bamboo charcoal | 10 | ethanol | 27 | 63 |
| Comp. Ex. 2 | HPMC | 10.00 | 0.00 | water | 90.0 | 100.0:0.0 | bamboo charcoal | 10 | ethanol | 27 | 63 |
| Comp. Ex. 3 | — | 0.00 | 10.00 | water | 90.0 | 0.0:100.0 | bamboo charcoal | 10 | ethanol | 27 | 63 |

TABLE 2

|  | evaluation of ink affinity | | | | evaluation of ink bleed | | | | evaluation of glossiness | |
|---|---|---|---|---|---|---|---|---|---|---|
|  | initial contact angle | | timewise change ratio of contact angles | | initial contact width | | timewise change ratio of contact widths | | | |
|  | (°) | evaluation | (%) | evaluation | μm | evaluation | (%) | evaluation | value | evaluation |
| Example 1 | 62.98 | ordinary | 23.6 | good | 0.68 | ordinary | 16.0 | good | 4.3 | ordinary |
| Example 2 | 62.52 | ordinary | 19.0 | ordinary | 0.72 | ordinary | 19.7 | good | 4.2 | ordinary |
| Example 3 | 60.50 | ordinary | 18.8 | ordinary | 0.73 | ordinary | 20.6 | ordinary | 4.2 | ordinary |
| Comp. Ex. 1 | 57.62 | bad | 18.4 | ordinary | 0.74 | ordinary | 22.2 | bad | 4.1 | ordinary |
| Comp. Ex. 2 | 83.07 | good | 15.9 | bad | 0.65 | good | 17.9 | good | 4.7 | good |
| Comp. Ex. 3 | 32.14 | bad | 16.3 | ordinary | 0.86 | bad | 18.9 | good | 3.5 | bad |

In each of Examples 1, 2 and 3, where the coating layer contained a water-soluble cellulose ether and PVA at a predetermined mass ratio, the coating layer had good ink affinity, suppressed ink bleed, and good glossiness.

On the other hand, in Comparative Example 1, where the coating layer contained a water-soluble cellulose ether and PVA at the mass ratio outside the specified range, the ink affinity at the end of measurement and glossiness were good, but the inferior initial ink affinity and the continuous ink bleed were observed. Further, in Comparative Example 2, where the coating layer contained only water-soluble cellulose ether, the timewise change ratio of contact widths was good so that the ink bleed was suppressed, but the timewise change ratio of contact angles was small, resulting in poor ink affinity. In Comparative Example 3, where the coating layer contained only PVA, the initial contact angle was small so that the ink droplet was immediately flattened, and the large initial contact width resulted in ink bleed, and the glossiness was not sufficient.

It is evident from the results of Examples 1, 2 and 3 that as the content of the water-soluble cellulose ether increases, the ink affinity is further improved.

The invention claimed is:

1. A method for producing a tablet marked with aqueous ink, comprising:
   a coating step of coating an object with a composition comprising
      a water-soluble cellulose ether having a viscosity at 20° C. of from 2.0 to 50.0 mPa·s, as determined in a 2% by mass aqueous solution thereof,
      polyvinyl alcohol, and
      a solvent,
   wherein a mass ratio of the water-soluble cellulose ether to the polyvinyl alcohol is from 99.0:1.0 to 55.0:45.0, to form a coating layer on the object; and
   a printing step of inkjet-printing on the coating layer with the aqueous ink to obtain the tablet marked with the aqueous ink.

2. The method according to claim 1, wherein the object is a core comprising an active ingredient.

3. The method according to claim 2, wherein the aqueous ink contains a pigment.

4. The method according to claim 1, wherein the water-soluble cellulose ether is selected from the group consisting of an alkyl cellulose, a hydroxyalkyl cellulose, and a hydroxyalkyl alkyl cellulose.

5. The method according to claim 1, wherein the polyvinyl alcohol has a degree of saponification of 74.0 mol % or more.

6. The method according to claim 1, wherein the solvent is selected from the group consisting of water and lower alcohols having 1 to 3 carbon atoms.

7. A tablet marked with aqueous ink, the tablet comprising:
   a coating layer comprising a water-soluble cellulose ether having a viscosity at 20° C. of from 2.0 to 50.0 mPa·s, as determined in a 2% by mass aqueous solution thereof, and polyvinyl alcohol, wherein the mass ratio of the water-soluble cellulose ether to the polyvinyl alcohol is from 99.0:1.0 to 55.0:45; and
   a mark with the aqueous ink on the coating layer.

8. The tablet marked with aqueous ink according to claim 7, wherein the water-soluble cellulose ether is selected from the group consisting of an alkyl cellulose, a hydroxyalkyl cellulose, and a hydroxyalkyl alkyl cellulose.

9. The tablet marked with aqueous ink according to claim 7, wherein the polyvinyl alcohol has a degree of saponification of 74.0 mol % or more.

* * * * *